(12) United States Patent
Hintzer et al.

(10) Patent No.: US 7,838,608 B2
(45) Date of Patent: Nov. 23, 2010

(54) FLUORINATED SURFACTANTS FOR MAKING FLUOROPOLYMERS

(75) Inventors: Klaus Hintzer, Kastl (DE); Michael Jürgens, Neuoetting (DE); Harald Kaspar, Burgkirchen (DE); Herbert Königsmann, Burgkirchen (DE); Andreas R Maurer, Langenneufnach (DE); Werner Schwertfeger, Altoetting (DE); Tilman C. Zipplies, Burghausen (DE)

(73) Assignee: 3M Innovative Properties Company, St. Paul, MN (US)

( * ) Notice: Subject to any disclaimer, the term of this patent is extended or adjusted under 35 U.S.C. 154(b) by 0 days.

(21) Appl. No.: 11/612,502

(22) Filed: Dec. 19, 2006

(65) Prior Publication Data

US 2007/0142541 A1 Jun. 21, 2007

(30) Foreign Application Priority Data

Dec. 21, 2005 (GB) ................................ 0525978.3

(51) Int. Cl.
*C08F 12/20* (2006.01)
(52) U.S. Cl. .................. 526/242; 526/214; 562/586; 524/544; 524/805; 427/180
(58) Field of Classification Search ................. 526/242, 526/214; 562/586; 524/544, 805
See application file for complete search history.

(56) References Cited

U.S. PATENT DOCUMENTS

| | | | |
|---|---|---|---|
| 2,713,593 A | 7/1955 | Brice et al. |
| 3,037,953 A | 6/1962 | Marks et al. |
| 3,142,665 A | 7/1964 | Cardinal et al. |
| 3,179,614 A | 4/1965 | Edwards |
| 3,260,691 A | 7/1966 | Lavin et al. |
| 3,271,341 A | 9/1966 | Garrison |
| 3,315,201 A | 4/1967 | Werme |
| 3,345,317 A | 10/1967 | Hoashi |
| 3,391,099 A | 7/1968 | Punderson |
| 3,451,908 A | 6/1969 | Sianesi et al. |
| 3,489,595 A | 1/1970 | Brown, Jr. |
| 3,555,100 A | 1/1971 | Garth et al. |
| 3,635,926 A | 1/1972 | Gresham |
| 3,642,742 A | 2/1972 | Carlson |
| 3,721,696 A | 3/1973 | Sianesi et al. |
| 3,790,403 A | 2/1974 | Ribbans, III |
| 3,855,191 A | 12/1974 | Doughty, Jr. et al. |
| 3,882,153 A | 5/1975 | Seki et al. |
| 3,981,945 A | 9/1976 | Attwood et al. |
| 4,016,345 A | 4/1977 | Holmes |
| 4,025,709 A | 5/1977 | Blaise et al. |
| 4,049,863 A | 9/1977 | Vassiliou |
| 4,123,401 A | 10/1978 | Berghmans et al. |
| 4,131,711 A | 12/1978 | Attwood |
| 4,252,859 A | 2/1981 | Concannon et al. |
| 4,262,101 A | 4/1981 | Hartwimmer et al. |
| 4,282,162 A | 8/1981 | Kuhls |
| 4,287,112 A | 9/1981 | Berghmans |
| 4,292,402 A | 9/1981 | Pollet et al. |
| 4,342,825 A | 8/1982 | Van Poucke et al. |
| 4,353,950 A | 10/1982 | Vassiliou |
| 4,369,266 A | 1/1983 | Kuhls et al. |
| 4,380,618 A | 4/1983 | Khan et al. |
| 4,381,384 A | 4/1983 | Khan |
| 4,391,940 A | 7/1983 | Kuhls et al. |
| 4,425,448 A | 1/1984 | Concannon et al. |
| 4,439,385 A | 3/1984 | Kuhls et al. |
| 4,544,458 A | 10/1985 | Grot et al. |
| 4,548,986 A | 10/1985 | Suzuki et al. |
| 4,552,925 A | 11/1985 | Nakagawa et al. |
| 4,588,796 A | 5/1986 | Wheland |
| 4,618,641 A | 10/1986 | Hengel |
| 4,621,116 A | 11/1986 | Morgan |
| 4,623,487 A | 11/1986 | Cope |
| 4,766,190 A | 8/1988 | Morita et al. |
| 4,789,717 A | 12/1988 | Giannetti et al. |
| 4,832,879 A | 5/1989 | Hamprecht |
| 4,861,845 A | 8/1989 | Slocum et al. |
| 4,864,006 A | 9/1989 | Giannetti et al. |
| 4,987,254 A | 1/1991 | Schwertfeger et al. |
| 5,075,397 A | 12/1991 | Tonelli et al. |

(Continued)

FOREIGN PATENT DOCUMENTS

CA 2354138 6/2000

(Continued)

OTHER PUBLICATIONS

Hu et al., "High Nucleophiicity of Formate Toward Polyhalofluoroalkenes", Chinese Chemical Letters, 1992, vol. 3, No. 2, pp. 87-92.*

(Continued)

*Primary Examiner*—Mark Eashoo
*Assistant Examiner*—Nicol M Buie-Hatcher
(74) *Attorney, Agent, or Firm*—Dena M. Ehrich; Brian E. Szymanski

(57) ABSTRACT

The invention provides a fluorinated surfactant having the general formula:

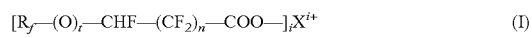

wherein $R_f$ represents a partially or fully fluorinated aliphatic group optionally interrupted with one or more oxygen atoms, t is 0 or 1 and n is 0 or 1, $X^{i+}$ represents a cation having a valence i and i is 1, 2 or 3. The surfactant can be used in emulsion polymerization of fluoromonomers to prepare fluoropolymers.

11 Claims, No Drawings

U.S. PATENT DOCUMENTS

| | | | |
|---|---|---|---|
| 5,153,322 A | 10/1992 | Flynn | |
| 5,160,791 A | 11/1992 | Tannenbaum | |
| 5,168,107 A | 12/1992 | Tannenbaum | |
| 5,182,342 A | 1/1993 | Feiring et al. | |
| 5,198,491 A | 3/1993 | Honda et al. | |
| 5,219,910 A | 6/1993 | Stahl et al. | |
| 5,223,343 A | 6/1993 | Tannenbaum | |
| 5,229,480 A | 7/1993 | Uschold | |
| 5,230,961 A | 7/1993 | Tannenbaum | |
| 5,272,186 A | 12/1993 | Jones | |
| 5,285,002 A | 2/1994 | Grootaert | |
| 5,312,935 A | 5/1994 | Mayer et al. | |
| 5,442,097 A | 8/1995 | Obermeier et al. | |
| 5,447,982 A | 9/1995 | Kamba et al. | |
| 5,453,477 A | 9/1995 | Oxenrider et al. | |
| 5,463,021 A | 10/1995 | Beyer et al. | |
| 5,478,651 A | 12/1995 | Tannenbaum | |
| 5,488,142 A | 1/1996 | Fall et al. | |
| 5,498,680 A | 3/1996 | Abusleme et al. | |
| 5,530,078 A | 6/1996 | Felix et al. | |
| 5,532,310 A | 7/1996 | Grenfell et al. | |
| 5,562,991 A | 10/1996 | Tannenbaum | |
| 5,576,381 A | 11/1996 | Bladel et al. | |
| 5,591,877 A | 1/1997 | Obermeier et al. | |
| 5,608,022 A | 3/1997 | Nakayama et al. | |
| 5,656,201 A | 8/1997 | Visca et al. | |
| 5,663,255 A | 9/1997 | Anolick et al. | |
| 5,667,846 A | 9/1997 | Thomas | |
| 5,688,884 A | 11/1997 | Baker et al. | |
| 5,700,859 A | 12/1997 | Ogura et al. | |
| 5,710,345 A | 1/1998 | Navarrini et al. | |
| 5,721,053 A | 2/1998 | Thomas | |
| 5,763,552 A | 6/1998 | Feiring et al. | |
| 5,789,083 A | 8/1998 | Thomas | |
| 5,789,508 A | 8/1998 | Baker et al. | |
| 5,804,650 A | 9/1998 | Tsuda et al. | |
| 5,895,799 A | 4/1999 | Wu et al. | |
| 5,955,556 A | 9/1999 | McCarthy et al. | |
| 5,959,026 A | 9/1999 | Abusleme et al. | |
| 5,969,063 A | 10/1999 | Parker et al. | |
| 5,990,330 A | 11/1999 | Sulzbach et al. | |
| 6,013,795 A | 1/2000 | Manzara et al. | |
| 6,025,307 A | 2/2000 | Chittofrati et al. | |
| 6,037,399 A | 3/2000 | Wu et al. | |
| 6,103,843 A | 8/2000 | Abusleme et al. | |
| 6,103,844 A | 8/2000 | Brothers | |
| 6,126,849 A | 10/2000 | Yamana et al. | |
| 6,136,893 A | 10/2000 | Yamashita et al. | |
| 6,153,688 A | 11/2000 | Miura et al. | |
| 6,218,464 B1 | 4/2001 | Parker et al. | |
| 6,245,923 B1 | 6/2001 | Sulzbach et al. | |
| 6,255,384 B1 | 7/2001 | McCarthy et al. | |
| 6,255,536 B1 | 7/2001 | Worm et al. | |
| 6,267,865 B1 | 7/2001 | Polson et al. | |
| 6,365,684 B1 | 4/2002 | McCarthy et al. | |
| 6,391,182 B2 | 5/2002 | Smeltzer et al. | |
| 6,395,848 B1 | 5/2002 | Morgan et al. | |
| 6,410,626 B1 | 6/2002 | Wada et al. | |
| 6,429,258 B1 | 8/2002 | Morgan et al. | |
| 6,436,244 B1 | 8/2002 | Fuhrer et al. | |
| 6,482,979 B1 | 11/2002 | Hintzer et al. | |
| 6,512,063 B2 | 1/2003 | Tang | |
| 6,518,442 B1 | 2/2003 | Felix et al. | |
| 6,576,703 B2 | 6/2003 | Kapeliouchko et al. | |
| 6,593,416 B2 | 7/2003 | Grootaert et al. | |
| 6,602,968 B1 | 8/2003 | Bekiarian et al. | |
| 6,610,788 B1 | 8/2003 | Takakura et al. | |
| 6,613,941 B1 | 9/2003 | Felix et al. | |
| 6,624,268 B1 | 9/2003 | Maekawa et al. | |
| 6,632,508 B1 | 10/2003 | Pellerite et al. | |
| 6,642,307 B1 | 11/2003 | Sogabe et al. | |
| 6,642,415 B1 | 11/2003 | Fuhrer et al. | |
| 6,660,798 B1 | 12/2003 | Marchese et al. | |
| 6,677,414 B2 | 1/2004 | Hintzer et al. | |
| 6,693,152 B2 | 2/2004 | Kaspar et al. | |
| 6,703,520 B2 | 3/2004 | Hintzer et al. | |
| 6,706,193 B1 | 3/2004 | Burkard et al. | |
| 6,710,123 B1 | 3/2004 | Amin-Sanayei et al. | |
| 6,737,489 B2 | 5/2004 | Linert et al. | |
| 6,750,304 B2 | 6/2004 | Kaspar et al. | |
| 6,761,964 B2 | 7/2004 | Tannenbaum | |
| 6,774,164 B2 | 8/2004 | Lyons et al. | |
| 6,794,550 B2 | 9/2004 | Hintzer et al. | |
| 6,815,040 B2 | 11/2004 | Pellerite et al. | |
| 6,822,059 B2 | 11/2004 | Buckanin et al. | |
| 6,825,250 B2 | 11/2004 | Epsch et al. | |
| 6,833,403 B1 | 12/2004 | Baldel et al. | |
| 6,846,570 B2 | 1/2005 | Leech et al. | |
| 6,861,466 B2 | 3/2005 | Dadalas et al. | |
| 6,861,490 B2 | 3/2005 | Kaspar et al. | |
| 6,869,997 B2 | 3/2005 | Wille et al. | |
| 6,878,772 B2 | 4/2005 | Visca et al. | |
| 6,956,078 B2 | 10/2005 | Cavanaugh et al. | |
| 6,972,094 B2 | 12/2005 | Ichida et al. | |
| 7,026,036 B2 | 4/2006 | Leech et al. | |
| 7,041,728 B2 | 5/2006 | Zipplies et al. | |
| 7,045,571 B2 | 5/2006 | Tan et al. | |
| 7,064,170 B2 | 6/2006 | Kaspar et al. | |
| 7,074,862 B2 | 7/2006 | Kaspar et al. | |
| 7,122,608 B1 | 10/2006 | Brinati et al. | |
| 7,125,941 B2 | 10/2006 | Kaulbach et al. | |
| 7,126,016 B2 | 10/2006 | Fu et al. | |
| 7,141,620 B2 | 11/2006 | Hoshikawa et al. | |
| 2001/0041740 A1* | 11/2001 | Matsumoto et al. | 514/520 |
| 2002/0198345 A1 | 12/2002 | Grootaert et al. | |
| 2003/0125421 A1 | 7/2003 | Bladel et al. | |
| 2004/0010156 A1 | 1/2004 | Kondo et al. | |
| 2004/0116742 A1 | 6/2004 | Guerra | |
| 2004/0143052 A1 | 7/2004 | Epsch et al. | |
| 2004/0186219 A1 | 9/2004 | Dadalas et al. | |
| 2004/0242755 A1 | 12/2004 | Araki et al. | |
| 2005/0043471 A1 | 2/2005 | Epsch et al. | |
| 2005/0070633 A1 | 3/2005 | Epsch et al. | |
| 2005/0090601 A1 | 4/2005 | Dadalas et al. | |
| 2005/0090613 A1 | 4/2005 | Maruya et al. | |
| 2005/0107506 A1 | 5/2005 | Kapeliouchko et al. | |
| 2005/0113519 A1 | 5/2005 | Buckanin et al. | |
| 2005/0154104 A1 | 7/2005 | Malvasi et al. | |
| 2005/0228127 A1 | 10/2005 | Tatemoto et al. | |
| 2006/0003168 A1 | 1/2006 | Dadalas et al. | |
| 2006/0041051 A1 | 2/2006 | Nakatani et al. | |
| 2006/0160947 A1 | 7/2006 | Tan et al. | |
| 2006/0281946 A1 | 12/2006 | Morita et al. | |
| 2007/0015864 A1 | 1/2007 | Hintzer et al. | |
| 2007/0025902 A1 | 2/2007 | Hintzer et al. | |
| 2007/0082993 A1 | 4/2007 | Amin-Sanayei et al. | |
| 2007/0117915 A1 | 5/2007 | Funaki et al. | |
| 2007/0135558 A1 | 6/2007 | Tsuda et al. | |
| 2007/0149733 A1 | 6/2007 | Otsuka et al. | |
| 2007/0155891 A1 | 7/2007 | Tsuda et al. | |

FOREIGN PATENT DOCUMENTS

| | | |
|---|---|---|
| DE | 3828063 | 2/1990 |
| DE | 19932771 | 1/2001 |
| DE | 19933696 | 1/2001 |
| DE | 10018853 | 10/2001 |
| EP | 0014431 | 8/1980 |
| EP | 0015481 | 9/1980 |
| EP | 0022257 | 1/1981 |
| EP | 0222945 | 11/1984 |
| EP | 0219065 | 4/1987 |
| EP | 0524585 | 1/1993 |
| EP | 0525660 | 2/1993 |

| | | |
|---|---|---|
| EP | 0612770 | 8/1994 |
| EP | 0625526 | 11/1994 |
| EP | 0632009 | 1/1995 |
| EP | 0649863 | 4/1995 |
| EP | 0712882 | 5/1996 |
| EP | 0718364 | 6/1996 |
| EP | 0739960 | 10/1996 |
| EP | 0752432 | 1/1997 |
| EP | 0816397 | 1/1998 |
| EP | 0818506 | 1/1998 |
| EP | 0890592 B1 | 1/1999 |
| EP | 0894541 | 2/1999 |
| EP | 0964009 | 12/1999 |
| EP | 0969027 | 1/2000 |
| EP | 1059333 | 12/2000 |
| EP | 1059342 | 12/2000 |
| EP | 1083441 | 3/2001 |
| EP | 1160258 | 12/2001 |
| EP | 1323677 | 7/2003 |
| EP | 1364972 | 11/2003 |
| EP | 1 334 996 | 3/2004 |
| EP | 1462461 | 9/2004 |
| EP | 1514848 | 4/2006 |
| GB | 642025 | 8/1950 |
| GB | 821353 | 10/1959 |
| GB | 966814 | 8/1964 |
| JP | 46011031 | 8/1966 |
| JP | 2000-128934 | 5/2000 |
| JP | 2002-179870 | 6/2002 |
| JP | 2002-308914 | 10/2002 |
| JP | 2002-317003 | 10/2002 |
| JP | 2003-043625 | 2/2003 |
| JP | 2003-119204 | 4/2003 |
| JP | 2003-212919 | 7/2003 |
| JP | 2004-359397 | 12/2004 |
| JP | 2004-359870 | 12/2004 |
| JP | 2005-008775 | 1/2005 |
| JP | 2005-0105045 | 4/2005 |
| RU | 2158274 | 10/2000 |
| WO | WO 94/14904 | 7/1994 |
| WO | WO96/24622 | 8/1996 |
| WO | WO 97/17381 | 5/1997 |
| WO | WO 98/50603 | 11/1998 |
| WO | WO 00/22002 | 4/2000 |
| WO | WO 00/35971 | 6/2000 |
| WO | WO 00/52060 | 9/2000 |
| WO | WO 00/71590 | 11/2000 |
| WO | WO 01/46116 | 6/2001 |
| WO | WO 01/79332 | 10/2001 |
| WO | WO 02/14223 | 2/2002 |
| WO | WO02/20676 | 3/2002 |
| WO | WO 02/078862 | 10/2002 |
| WO | WO 02/088203 | 11/2002 |
| WO | WO 02/088206 | 11/2002 |
| WO | WO 02/088207 | 11/2002 |
| WO | WO 02/095121 | 11/2002 |
| WO | WO 03/020836 | 3/2003 |
| WO | WO 03/051988 | 6/2003 |
| WO | WO 03/087176 | 10/2003 |
| WO | WO 03/087179 | 10/2003 |
| WO | WO 2004/031141 | 4/2004 |
| WO | WO 2004/067588 | 8/2004 |
| WO | WO 2005/003075 | 1/2005 |
| WO | WO2005/042593 | 5/2005 |
| WO | WO2005/056614 | 6/2005 |
| WO | WO2005/063827 | 7/2005 |
| WO | WO2005/065800 | 7/2005 |
| WO | WO 2005/082785 | 9/2005 |
| WO | WO2005/121290 | 12/2005 |
| WO | WO2006/011533 | 2/2006 |
| WO | WO2006/020721 | 2/2006 |
| WO | WO 2007/120348 | 10/2007 |

OTHER PUBLICATIONS

LaZerte et al., "The Free-radical Catalyzed Addition of Alcohols and Aldehydes to Perfluoroolefins", J. Am. Chem. Soc., 1955, 77, pp. 910-914.*
"Guide to Protein Purification, Methods in Enzymology," Deutscher, M. vol. 182, 24. 1990. (pp. 309-317).
"High Performance Polymers for Diverse Applications," Modern Fluoropolymers Edited by John Scheirs. John Wiley & Sons, 1997.
"Hydrogen-Ion Activity to Laminated Materials, Glass," Encyclopedia of Chemical Technology. John Wiley & Sons, vol. 13, $3^{rd}$ Ed. 1981. (p. 687).
"Immobilized Biocatalysts to Isoprene," Ullmann's Encyclopedia of Industrial Chemistry. vol. A14. 1985. (p. 439-459).
"Identification to Lignin," Encyclopedia of Polymer Science and Engineering. John Wiley & Sons, vol. 8. 1987 (p. 347).
"Nonionic Surfactants." Edited by Martin J. Schick. 1967.
"Synthesis of Perfluoroalkyl Vinyl Ether Acids and Derivatives," Perfluoroalkyl Vinyl Ether Acids. Raymond Sullivan, vol. 34, No. 6, Jun. 1969. (p. 1841).
Drobny, Technology of Fluoropolymers, CRC Press LLC, 2001, p. 35.
England, "Catalytic Conversion of Fluoroalkyl Alkyl Ethers to Carbonyl Compounds", J. Org. Chem., 1984, vol. 49, pp. 4007-4008.
Sudol et al., "Miniemulsion Polymerization", Emulsion Polymerization and Emulsion Polymers, John Wiley & Sons, 1997, Chapter. 20.
Candau, "Inverse Emulsion and Microemulsion Polymerization", Emulsion Polymerization and Emulusion Polymers, John Wiley & Sons, 1997, Chapter 21.
Chi et al., "A Facile Synthesis of Partly-fluorinated Ethers Using Perfluroporpoxyethylene and Aliphatic Alcohols", Bull. Korean Chem. Soc., 1999, vol. 20, No. 2, pp. 220-222.
Ebnesajjad, "Fluoroplastics, vol. 1, Non-Melt Processible Fluoroplastics", Plastics Design Library, NY, 2000, pp. 285-295.
Ebnesajjad, "Fluoroplastics, vol. 2, Melt Processible Fluoropolymers", Plastics Design Library, NY, 2003, pp. 1-21.
ASTM D 4895-04, "Standard Specification for Polytetrafluoroethylene (PTFE) Resin Produced From Dispersion", pp. 1-14.
Storsberg, Joachim and Ritter, Helmut, "Cyclodextrins in Polymer Synthesis: A 'Green' Route to Fluorinated Polymers via Cyclodextrin Complexes in Aqueous Solution", Macromol. Chem Phys., 2002, pp. 812-818.
Kokelenberg, H. and Pollet, R., "A New type fluortensides, based on the addition of nucleophiles to chlorotrifluoroethylene and hexafluoropropylene." Tenside Detergents, 1985, 22(1), pp. 22-27.
Apostolo et al., "Microemulsion Polymerization for Producing Fluorinated Structured Materials", Macromol. Symp. 2004, 206, pp. 347-360.
Ivanova et al., "Synthesis of Alcohols from Perfluorvinyl Esters", Zh. Vses. Khim Obsh 1999, (24), pp. 656-657.
W.C. Griffin "Calculation of HLB Values of Non-Ionic Surfactants", Journal of Society of Cosmetic Chemists, vol. 5, (1954) p. 259.

* cited by examiner

FLUORINATED SURFACTANTS FOR MAKING FLUOROPOLYMERS

CROSS REFERENCE TO RELATED APPLICATION

This application claims priority to Great Britain Patent Application No. 0525978.3, filed on Dec. 21, 2005, the disclosure of which is herein incorporated by reference in its entirety.

FIELD OF THE INVENTION

The present invention relates to fluorinated surfactants and in particular relates to fluorinated surfactants that are suitable for use in the aqueous emulsion polymerization of fluorinated monomers to produce fluoropolymers.

BACKGROUND OF THE INVENTION

Fluoropolymers, i.e. polymers having a fluorinated backbone, have been long known and have been used in a variety of applications because of several desirable properties such as heat resistance, chemical resistance, weatherability, UV-stability etc. The various fluoropolymers are for example described in "Modern Fluoropolymers", edited by John Scheirs, Wiley Science 1997. Commonly known or commercially employed fluoropolymers include polytetrafluoroethylene (PTFE), copolymers of tetrafluoroethylene (TFE) and hexafluoropropylene (HFP) (FEP polymers), perfluoroalkoxy copolymers (PFA), ethylene-tetrafluoroethylene (ETFE) copolymers, terpolymers of tetrafluoroethylene, hexafluoropropylene and vinylidene fluoride (VDF) (so called THV copolymers) and polyvinylidene fluoride polymers (PVDF). Commercially employed fluoropolymers also include fluoroelastomers and thermoplastic fluoropolymers.

Several methods are known to produce fluoropolymers. Such methods include suspension polymerization, aqueous emulsion polymerization, solution polymerization, polymerization using supercritical $CO_2$, and polymerization in the gas phase.

Currently, the most commonly employed polymerization methods include suspension polymerization and especially aqueous emulsion polymerization. The aqueous emulsion polymerization normally involves the polymerization in the presence of a fluorinated surfactant, which is generally used for the stabilization of the polymer particles formed. The suspension polymerization generally does not involve the use of surfactant but results in substantially larger polymer particles than in case of the aqueous emulsion polymerization. Thus, the polymer particles in case of suspension polymerization will quickly settle out whereas in case of dispersions obtained in emulsion polymerization generally good stability over a long period of time is obtained.

It is generally recognized that an aqueous emulsion polymerization wherein no surfactant is used to generally produce homo- and copolymers of chlorotrifluoroethylene (CTFE).

Notwithstanding the fact that emulsifier free polymerizations are known, the aqueous emulsion polymerization process in the presence of fluorinated surfactants is still a desirable process to produce fluoropolymers because it can yield stable fluoropolymer particle dispersions in high yield and in a more environmental friendly way than for example polymerizations conducted in an organic solvent. Frequently, the emulsion polymerization process is carried out using a perfluoroalkanoic acid or salt thereof as a surfactant. These surfactants are typically used as they provide a wide variety of desirable properties such as high speed of polymerization, good copolymerization properties of fluorinated olefins with comonomers, small particle sizes of the resulting dispersion can be achieved, good polymerization yields i.e. a high amount of solids can be produced, good dispersion stability, etc. However, environmental concerns have been raised against these surfactants and moreover these surfactants are generally expensive. Alternative surfactants to the perfluoroalkanoic acids or salts thereof have also been proposed in the art for conducting the emulsion polymerization of fluorinated monomers.

It would now be desirable to find an alternative emulsion polymerization process in which the use of perfluoroalkanoic acids and salts thereof as a fluorinated surfactant can be avoided. In particular, it would be desirable to find an alternative surfactant or dispersant, in particular one that is more environmentally friendly, for example has a low toxicity and/or shows no or only little bioaccumulation. It would also be desirable that the alternative surfactant has good chemical and thermal stability enabling polymerization over a wide range of conditions of for example temperature and/or pressure. Desirably, the alternative surfactant or dispersant allows for a high polymerization rate, good dispersion stability, good yields, good copolymerization properties; less or no telogenic effects and/or the possibility of obtaining a wide variety of particle sizes including small particle sizes. The properties of the resulting fluoropolymer should generally not be negatively influenced and preferably would be improved. Desirably, the resulting dispersions have good or excellent properties in coating applications and/or impregnation of substrates, including for example good film forming properties. It would further be desirable that the polymerization can be carried out in a convenient and cost effective way, preferably using equipment commonly used in the aqueous emulsion polymerization of fluorinated monomers. Additionally, it may be desirable to recover the alternative surfactant or dispersant from waste water streams and/or to remove or recover the surfactant from the dispersion subsequent to the polymerization. Desirably, such recovery can proceed in an easy, convenient and cost effective way.

SUMMARY OF THE INVENTION

In accordance with one aspect of the present invention, there is provided a fluorinated surfactant having the general formula:

$$[R_f-(O)_t-CHF-(CF_2)_n-COO^-]_i X^{i+} \qquad (I)$$

wherein $R_f$ represents a partially or fully fluorinated aliphatic group optionally interrupted with one or more oxygen atoms, t is 0 or 1 and n is 0 or 1, $X^{i+}$ represents a cation having a valence i and i is 1, 2 or 3. Examples of cations $X^{i+}$ include $H^+$, ammonium such as $NH_4^+$, metal cations such as alkali metal ions including sodium and potassium and earth alkali cations such as calcium and magnesium. Generally, the fluorinated surfactant of formula (I) will be a low molecular weight compound, for example a compound having a molecular weight for the anion part of the compound of not more than 1000 g/mol, typically not more than 600 g/mol and in particular embodiments, the anion of the fluorinated surfactant may have a molecular weight of not more than 500 g/mol.

Particularly preferred fluorinated carboxylic acids are those that when administered to rats show a recovery of at least 45%, for example at least 50% of the administered amount after 96 hours via renal elimination and that have a renal elimination half-life of not more than 35 hours, for example of not more than 30 hours in rats as tested according to the method set forth in the examples. Generally, fluorinated carboxylic acids in which each of the fluorinated aliphatic moieties in the compound have not more than 3 carbon atoms fulfill the aforementioned conditions of renal recovery and half-life. Thus, preferred compounds are those in which any fluorinated alkylene groups have not more than 3 carbon atoms and in which a fluorinated alkyl group of the compound has not more than 3 carbon atoms.

It has been found that these surfactants can be easily and conveniently be prepared in a cost effective way. In particular, the fluorinated surfactants of formula (I) have been found to be suitable in the aqueous emulsion polymerization of monomers, in particular fluorinated monomers. In addition to their use in aqueous emulsion polymerization, the fluorinated surfactants may be useful in other applications where surfactants are used, such as for example in coating compositions or in stabilizing dispersions including for example fluoropolymer dispersions.

DETAILED DESCRIPTION

The fluorinated surfactant (I) can be derived from fluorinated olefins of the general formula:

$$R_f\text{—}(O)_t\text{—}CF\!=\!CF_2 \quad (II)$$

wherein $R_f$ and t are as defined above.

According to one embodiment, surfactants according to formula (I) wherein n is 0 can be prepared by reacting a fluorinated olefin of formula (II) with a base.

In an alternative embodiment to prepare the fluorinated surfactants of formula (I) wherein n is 0 can be prepared by reacting a fluorinated olefin of formula (II) with a hydrocarbon alcohol in an alkaline medium and then decomposing the resulting ether in acidic conditions thereby forming the corresponding carboxylic acid.

To prepare fluorinated surfactants of formula (I) wherein n is 1, a free radical reaction of the fluorinated olefin of formula (II) with a hydrocarbon alcohol is carried out followed by an oxidation of the resulting reaction product.

Still further, in a particular aspect, the invention provides a method for making a fluoropolymer comprising an aqueous emulsion polymerization of one or more fluorinated monomers wherein said aqueous emulsion polymerization is carried out in the presence of one or more fluorinated surfactants according to formula (I) above.

In yet a further aspect, the present invention provides an aqueous composition comprising one or more fluorinated surfactants according to formula (I) above.

In a still further aspect, the present invention provides a method of applying the above defined aqueous composition to a substrate. Suitable substrates include for example metal substrates, glass, plastic or fabrics.

Fluorinated surfactants according to formula (I) may be used in a variety of applications where a surfactant is needed or desired. The fluorinated surfactants according to formula (I) have been found to be suitable for use in an aqueous emulsion polymerization of fluorinated and/or non-fluorinated monomers. In particular, the fluorinated surfactants can be used in the aqueous emulsion polymerization of fluorinated monomers, e.g. fluorinated olefins, to make fluoropolymers that have a partially or fully fluorinated backbone.

The $R_f$ group in formula (I) above represents a partially or fully fluorinated aliphatic group that may be interrupted with one or more oxygen atoms. In a particular embodiment, the $R_f$ group will have from 1 to 50 carbon atoms, for example between 3 and 30 carbon atoms. Generally, a fully fluorinated $R_f$ group will be preferred when the surfactant is to be used in the aqueous emulsion polymerization of fluorinated monomers to make fluoropolymers with a partially or fully fluorinated backbone. Thus, for the aqueous emulsion polymerization, surfactants according to formula (I) are preferred in which $R_f$ is a perfluorinated aliphatic group optionally interrupted with one or more oxygen atoms. For environmental reasons, it will generally be preferred that a perfluorinated aliphatic $R_f$ group does not contain alkyl and/or alkylene fragments of more than 6 carbon atoms, preferably not more than 3 carbon atoms.

In a particular embodiment, the $R_f$ is selected from the group consisting of perfluorinated aliphatic groups of 1 to 6 carbon atoms, perfluorinated groups of the formula:

$$R_f^1\text{—}[OR_f^2]_p\text{—}[OR_f^3]_q\text{—}$$

wherein $R_f^1$ is a perfluorinated aliphatic group of 1 to 6 carbon atoms, for example up to 3 carbon atoms, $R_f^2$ and $R_f^3$ each independently represents linear or branched a perfluorinated alkylene of 1, 2, 3 or 4 carbon atoms and p and q each independently represent a value of 0 to 4 and wherein the sum of p and q is at least 1 and perfluorinated groups of the formula:

$$R_f^4\text{—}[OR_f^5]_k\text{—}[OR_f^6]_m\text{—}O\text{—}CF_2\text{—}$$

wherein $R_f^4$ is a perfluorinated aliphatic group of 1 to 3 or 4 carbon atoms, $R_f^5$ and $R_f^6$ each independently represents a linear or branched perfluorinated alkylene of 1, 2, 3 or 4 carbon atoms and k and m each independently represent a value of 0 to 4.

In yet a further embodiment, $R_f$ may correspond to the following formula:

$$R_f^8\text{—}(OCF_2)_a\text{—} \quad (III)$$

wherein a is an integer of 1 to 6 and $R_f^8$ is a linear partially fluorinated aliphatic group or a linear fully fluorinated aliphatic group having 1, 2, 3 or 4 carbon atoms. When $R_f^8$ is a partially fluorinated aliphatic group, the number of carbon atoms preferably is between 1 and 6 and the number of hydrogen atoms in the partially fluorinated aliphatic groups is preferably 1 or 2.

In a still further embodiment, $R_f$ may correspond to the following formula:

$$R_f^9\text{—}O\text{—}(CF_2)_b\text{—} \quad (IV)$$

wherein b is an integer of 1 to 6, preferably 1, 2, 3 or 4 and $R_f^9$ is a linear partially fluorinated aliphatic group or a linear fully fluorinated aliphatic group having 1, 2, 3 or 4 carbon atoms. When $R_f^9$ is a partially fluorinated aliphatic group, the number of carbon atoms preferably is between 1 and 6 and the number of hydrogen atoms in the partially fluorinated groups is preferably 1 or 2.

Specific examples of fluorinated surfactants according to formula (I) include:

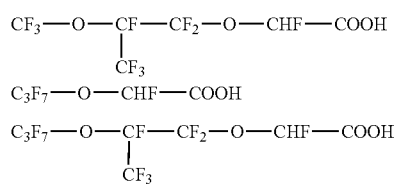

-continued

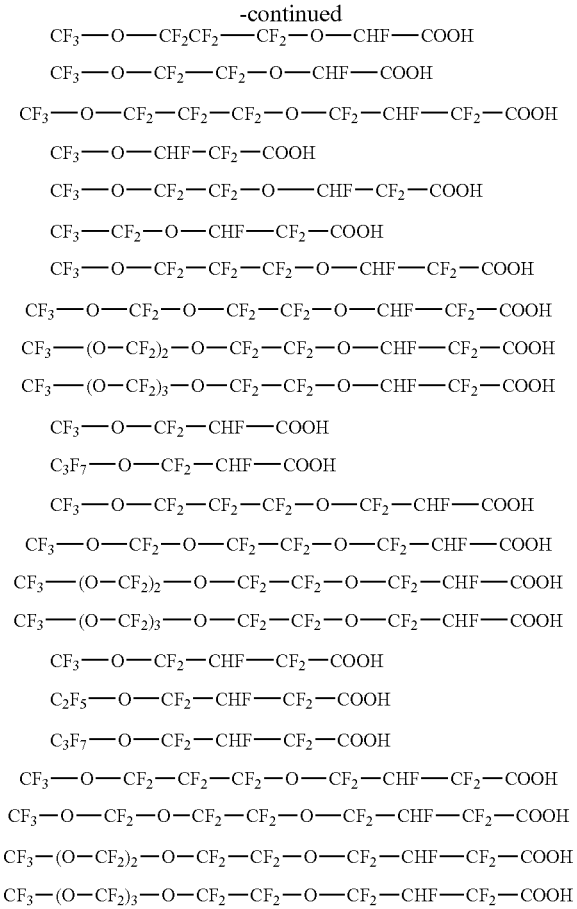

It is understood that while the above list of compounds only lists the acids, the corresponding salts, in particular the $NH_4^+$, potassium, sodium or lithium salts can equally be used.

The fluorinated surfactants can be derived from a fluorinated olefin of formula (II). Fluorinated olefins according to formula (II) that can be used to prepare the fluorinated surfactants of formula (I) include perfluorinated alkyl vinyl compounds, vinyl ethers in particular perfluorovinyl ethers and allyl ethers, in particular perfluorinated allyl ethers. Particular examples of fluorinated olefins include those that are used in the preparation of fluoropolymers and that are described below.

According to one embodiment, surfactants according to formula (I) wherein n is 0 can be prepared by reacting a fluorinated olefin of formula (II) with a base. The reaction is generally carried out in aqueous media. An organic solvent may be added to improve the solubility of the fluorinated olefin. Examples of organic solvents include glyme, tetrahydrofuran (THF) and acetonitrile. Additionally or alternatively a phase transfer catalyst may be used. As a base, use can be made of for example ammonia, alkali and earth alkali hydroxides. Without intending to be bound by any theory, it is believed, that the reaction proceeds according to the following sequence when ammonia is used as a base:

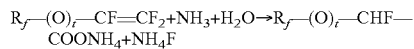

The reaction is generally carried out between 0 and 200° C., for example between 20-150° C. and at a pressure between about 1 bar up to about 20 bar. For further purification, the obtained salts can be distilled via the free acid or by first converting the acid into an ester derivative and then distilling the ester derivative followed by hydolysis of the ester to obtain the purified acid or salt thereof.

In an alternative embodiment to prepare the fluorinated surfactants of formula (I) wherein n is 0 can be prepared by reacting a fluorinated olefin of formula (II) with a hydrocarbon alcohol in an alkaline medium and then decomposing the resulting ether in acidic conditions thereby forming the corresponding carboxylic acid. Suitable hydrocarbon alcohols include aliphatic alcohols such as lower alkanols having 1 to 4 carbon atoms. Specific examples include methanol, ethanol and butanol including t-butanol. The reaction of the fluorinated olefin with the alcohol in an alkaline medium may be carried out as described in "Furin et al., Bull Korean Chem. Soc. 20, 220 [1999]". The reaction product of this reaction is an ether derivative of the fluorinated olefin. This resulting ether can be decomposed under acidic conditions as described in "D. C. England, J. Org. Chem. 49, 4007 (1984)" to yield the corresponding carboxylic acid or salt thereof.

To prepare fluorinated surfactants of formula (I) wherein n is 1, a free radical reaction of the fluorinated olefin of formula (II) with a hydrocarbon alcohol may be carried out followed by an oxidation of the resulting reaction product. Suitable hydrocarbon alcohols that can be used include aliphatic alcohols such as lower alkanols having 1 to 4 carbon atoms. Specific examples include methanol, ethanol and propanol. The free radical reaction is typically carried out using a free radical initiator as is typically used in a free radical polymerization reaction. Examples of suitable free radical initiators include persulfates such as for example ammonium persulfate. Detailed conditions of the free radical reaction of the fluorinated surfactant with an alcohol can be found in "S. V. Sokolov et al., Zh. Vses. Khim Obsh 24, 656 (1979)". The resulting alcohol derivative of the fluorinated olefin can be chemically oxidized with an oxidizing agent to the corresponding carboxylic acid. Examples of oxidizing agents include for example potassium permanganate, chromium (VI) oxide, $RuO_4$ or $OsO_4$ optionally in the presence of NaOCl, nitric acid/iron catalyst, dinitrogen tetroxide. Typically the oxidation is carried out in acidic or basic conditions at a temperature between 10 and 100° C. In addition to chemical oxidation, electrochemical oxidation may be used as well.

In a particular preferred embodiment, one or more fluorinated surfactants of formula (I) are used in the aqueous emulsion polymerization of one or more fluorinated monomers, in particular gaseous fluorinated monomers. By gaseous fluorinated monomers is meant monomers that are present as a gas under the polymerization conditions. In a particular embodiment, the polymerization of the fluorinated monomers is started in the presence of the fluorinated surfactant according to formula (I), i.e. the polymerization is initiated in the presence of the fluorinated surfactant. The amount of fluorinated surfactant used may vary depending on desired properties such as amount of solids, particle size etc. . . . Generally the amount of fluorinated surfactant will be between 0.001% by weight based on the weight of water in the polymerization and 5% by weight, for example between 0.005% by weight and 2% by weight. A practical range is between 0.05% by weight and 1% by weight. While the polymerization is generally initiated in the presence of the fluorinated surfactant, it is not excluded to add further fluorinated surfactant during the polymerization although such will generally not be necessary. Nevertheless, it may be desirable to add certain monomer to the polymerization in the form of an aqueous emulsion. For example, fluorinated monomers and in particular perfluorinated co-monomers that are liquid under the polymerization conditions may be advantageously added in the form of an aqueous emulsion. Such emulsion of such co-monomers is preferably prepared using the fluorinated surfactant according to formula (I) as an emulsifier.

In accordance with a particular embodiment of the present invention, a mixture of fluorinated surfactants according to formula (I) is used. In a still further embodiment the fluorinated surfactant according to formula (I) or mixture thereof may be used in combination with one or more further fluorinated surfactants that do not correspond to formula (I). In particular, such further fluorinated surfactants include perfluorinated ethers and perfluorinated polyethers. Suitable perfluorinated polyethers include those according to the following formulas (III) or (IV):

$$CF_3-(OCF_2)_m-O-CF_2-X \quad (III)$$

wherein m has a value of 1 to 6 and X represents a carboxylic acid group or salt thereof, $$CF_3-O-(CF_2)_3-(OCF(CF_3)-CF_2)_z-O-L-Y \quad (IV)$$

wherein z has a value of 0, 1, 2 or 3, L represents a divalent linking group selected from $$-CF(CF_3)-, -CF_2- \text{ and } -CF_2CF_2-$$

and Y represents a carboxylic acid group or salt thereof. Examples of carboxylic acid salts include sodium, potassium and ammonium ($NH_4$) salts. Still further polyethers include those disclosed in U.S. Pat. No. 3,271,341; U.S. Publication No. 2005/0090613; U.S. Pat. No. 4,864,006; U.S. Pat. No. 4,789,717 and EP 625526. Examples of perfluorinated ether surfactants that can be used include those according to the following general formula:

$$R^7_f-O-CF_2CF_2-X \quad (V)$$

wherein $R_f^7$ represents a linear or branched perfluoroalkyl group having 1, 2, 3 or 4 carbon atoms and X represents a carboxylic acid group or salt thereof. Examples of carboxylic acid salts include sodium, potassium and ammonium ($NH_4$) salts.

When the fluorinated surfactant(s) according to formula (I) are used in admixture with one or more further fluorinated surfactants, the fluorinated surfactant(s) of formula (I) may be present in a weight ratio of for example 1:10 to 100:1. Generally, when such a mixture is used it will be preferred that the fluorinated surfactant(s) according to formula (I) represents at least 20%, for example at least 30% or at least 51% by weight of the total amount of fluorinated surfactant used.

The aqueous emulsion polymerization may be carried out at a temperature between 10 to 150° C., preferably 20° C. to 110° C. and the pressure is typically between 2 and 30 bar, in particular 5 to 20 bar. The reaction temperature may be varied during the polymerization to influence the molecular weight distribution, i.e., to obtain a broad molecular weight distribution or to obtain a bimodal or multimodal molecular weight distribution.

The pH of the polymerization media may be in the range of pH 2-11, preferably 3-10, most preferably 4-10.

The aqueous emulsion polymerization is typically initiated by an initiator including any of the initiators known for initiating a free radical polymerization of fluorinated monomers. Suitable initiators include peroxides and azo compounds and redox based initiators. Specific examples of peroxide initiators include, hydrogen peroxide, sodium or barium peroxide, diacylperoxides such as diacetylperoxide, disuccinyl peroxide, dipropionylperoxide, dibutyrylperoxide, dibenzoylperoxide, benzoylacetylperoxide, diglutaric acid peroxide and dilaurylperoxide, and further per-acids and salts thereof such as e.g. ammonium, sodium or potassium salts. Examples of per-acids include peracetic acid. Esters of the peracid can be used as well and examples thereof include tert.-butylperoxyacetate and tert.-butylperoxypivalate. Examples of inorganic include for example ammonium-alkali- or earth alkali salts of persulfates, permanganic or manganic acid or manganic acids. A persulfate initiator, e.g. ammonium persulfate (APS), can be used on its own or may be used in combination with a reducing agent. Suitable reducing agents include bisulfites such as for example ammonium bisulfite or sodium metabisulfite, thiosulfates such as for example ammonium, potassium or sodium thiosulfate, hydrazines, azodicarboxylates and azodicarboxyldiamide (ADA). Further reducing agents that may be used include sodium formaldehyde sulfoxylate (Rongalit®) or fluoroalkyl sulfinates as disclosed in U.S. Pat. No. 5,285,002. The reducing agent typically reduces the half-life time of the persulfate initiator. Additionally, a metal salt catalyst such as for example copper, iron or silver salts may be added. The amount of initiator may be between 0.01% by weight (based on the fluoropolymer solids to be produced) and 1% by weight. In one embodiment, the amount of initiator is between 0.05 and 0.5% by weight. In another embodiment, the amount may be between 0.05 and 0.3% by weight.

The aqueous emulsion polymerization system may further comprise other materials, such as buffers and, if desired, complex-formers or chain-transfer agents. Examples of chain transfer agents that can be used include dimethyl ether, methyl t-butyl ether, alkanes having 1 to 5 carbon atoms such as ethane, propane and n-pentane, halogenated hydrocarbons such as $CCl_4$, $CHCl_3$ and $CH_2Cl_2$ and hydrofluorocarbon compounds such as $CH_2F-CF_3$ (R134a). Additionally esters like ethylacetate, malonic esters are applicable.

Examples of fluorinated monomers that may be polymerized using the fluorinated surfactant according to formula (I) as an emulsifier include partially or fully fluorinated gaseous monomers including fluorinated olefins such as tetrafluoroethylene (TFE), chlorotrifluoroethylene (CTFE), hexafluoropropylene (HFP), vinyl fluoride (VF), vinylidene fluoride (VDF), partially or fully fluorinated allyl ethers and partially or fully fluorinated vinyl ethers. The polymerization may further involve non-fluorinated monomers such as ethylene and propylene.

Further examples of fluorinated monomers that may be used in the aqueous emulsion polymerization according to the invention include those corresponding to the formula:

$$CF_2=CF-O-R_f$$

wherein $R_f$ represents a perfluorinated aliphatic group that may contain one or more oxygen atoms. Preferably, the perfluorovinyl ethers correspond to the general formula:

$$CF_2=CFO(R_fO)_n(R'_fO)_mR''_f$$

wherein $R_f$ and $R'_f$ are different linear or branched perfluoroalkylene groups of 2-6 carbon atoms, m and n are independently 0-10, and $R''_f$ is a perfluoroalkyl group of 1-6 carbon atoms. Examples of perfluorovinyl ethers according to the above formulas include perfluoro-2-propoxypropylvinyl ether (PPVE-2), perfluoro-3-methoxy-n-propylvinyl ether, perfluoro-2-methoxy-ethylvinyl ether, perfluoromethylvinyl ether (PMVE), perfluoro-n-propylvinyl ether (PPVE-1) and $CF_3-(CF_2)_2-O-CF(CF_3)-CF_2-O-F(CF_3)-CF_2-O-CF=CF_2$.

Examples of fluorinated allyl ethers that can be used include those corresponding to the general formula:

$$CF_2=CF-CF_2-O-R_f$$

wherein $R_f$ represents a perfluorinated aliphatic group that may contain one or more oxygen atoms.

Still further, the polymerization may involve comonomers that have a functional group such as for example a group capable of participating in a peroxide cure reaction. Such functional groups include halogens such as Br or I as well as nitrile groups. Specific examples of such comonomers that may be listed here include (a) bromo- or iodo-(per)fluoroalkyl-(per)fluorovinylethers having the formula:

$$Z-R_f-O-CX=CX_2$$

wherein each X may be the same or different and represents H or F, Z is Br or I, $R_f$ is a (per)fluoroalkylene $C_1$-$C_{12}$, optionally containing chlorine and/or ether oxygen atoms; for example: $BrCF_2-O-CF=CF_2$, $BrCF_2CF_2-O-CF=CF_2$, $BrCF_2CF_2CF_2-O-CF=CF_2$, $CF_3CFBrCF_2-O-CF=CF_2$, and the like; and (b) bromo- or iodo containing fluoroolefins such as those having the formula:

$$Z'-(R_f')_r-CX=CX_2,$$

wherein each X independently represents H or F, Z' is Br or I, $R_f'$ is a perfluoroalkylene $C_1$-$C_{12}$, optionally containing chlorine atoms and r is 0 or 1; for instance: bromotrifluoroethylene, 4-bromo-perfluorobutene-1, and the like; or bromofluoroolefins such as 1-bromo-2,2-difluoroethylene and 4-bromo-3,3,4,4-tetrafluorobutene-1.

Examples of nitrile containing monomers that may be used include those that correspond to one of the following formulas:

$$CF_2=CF-CF_2-O-R_f-CN$$

$$CF_2=CFO(CF_2)_LCN$$

$$CF_2=CFO[CF_2CF(CF_3)O]_g(CF_2)_vOCF(CF_3)CN$$

$$CF_2=CF[OCF_2CF(CF_3)]_kO(CF_2)_uCN$$

wherein L represents an integer of 2 to 12; g represents an integer of 0 to 4; k represents 1 or 2; v represents an integer of 0 to 6; u represents an integer of 1 to 6, $R_f$ is a perfluoroalkylene or a bivalent perfluoroether group. Specific examples of nitrile containing liquid fluorinated monomers include perfluoro(8-cyano-5-methyl-3,6-dioxa-1-octene), $CF_2=CFO(CF_2)_5CN$, and $CF_2=CFO(CF_2)_3OCF(CF_3)CN$.

The aqueous emulsion polymerization may be used to produce a variety of fluoropolymers including perfluoropolymers, which have a fully fluorinated backbone, as well as partially fluorinated fluoropolymers. Also the aqueous emulsion polymerization may result in melt-processible fluoropolymers as well as those that are not melt-processible such as for example polytetrafluoroethylene and so-called modified polytetrafluoroethylene. The polymerization process can further yield fluoropolymers that can be cured to make fluoroelastomers as well as fluorothermoplasts. Fluorothermoplasts are generally fluoropolymers that have a distinct and well noticeable melting point, typically in the range of 60 to 320° C. or between 100 and 320° C. They thus have a substantial crystalline phase. Fluoropolymers that are used for making fluoroelastomers typically are amorphous and/or have a neglectable amount of crystallinity such that no or hardly any melting point is discernable for these fluoropolymers.

The aqueous emulsion polymerization results in a dispersion of the fluoropolymer in water. Generally the amount of solids of the fluoropolymer in the dispersion directly resulting from the polymerization will vary between 3% by weight and about 40% by weight depending on the polymerization conditions. A typical range is between 5 and 30% by weight, for example between 10 and 25% by weight. The particle size (volume average diameter) of the fluoropolymer is typically between 40 nm and 400 nm with a typical particle size being between 60 nm and about 350 nm. The total amount of fluorinated surfactant according to formula (I) in the resulting dispersion is typically between 0.001 and 5% by weight based on the amount of fluoropolymer solids in the dispersion. A typical amount may be from 0.01 to 2% by weight or from 0.02 to 1% by weight.

The fluoropolymer may be isolated from the dispersion by coagulation if a polymer in solid form is desired. Also, depending on the requirements of the application in which the fluoropolymer is to be used, the fluoropolymer may be post-fluorinated so as to convert any thermally unstable end groups into stable $CF_3$ end groups. The fluoropolymer may be post-fluorinated as described in for example EP 222945. Generally, the fluoropolymer will be post fluorinated such that the amount of end groups in the fluoropolymer other than $CF_3$ is less than 80 per million carbon atoms.

For coating applications, an aqueous dispersion of the fluoropolymer is desired and hence the fluoropolymer will not need to be separated or coagulated from the dispersion. To obtain a fluoropolymer dispersion suitable for use in coating applications such as for example in the impregnation of fabrics or in the coating of metal substrates to make for example cookware, it will generally be desired to add further stabilizing surfactants and/or to further increase the fluoropolymer solids. For example, non-ionic stabilizing surfactants may be added to the fluoropolymer dispersion. Typically these will be added thereto in an amount of 1 to 12% by weight based on fluoropolymer solids. Examples of non-ionic surfactants that may be added include $$R^1-O-[CH_2CH_2O]_n-[R^2O]_m-R^3 \quad (VI)$$

wherein $R^1$ represents an aromatic or aliphatic hydrocarbon group having at least 8 carbon atoms, $R^2$ represents an alkylene having 3 carbon atoms, $R^3$ represents hydrogen or a $C_1$-$C_3$ alkyl group, n has a value of 0 to 40, m has a value of 0 to 40 and the sum of n+m being at least 2. It will be understood that in the above formula (VI), the units indexed by n and m may appear as blocks or they may be present in an alternating or random configuration. Examples of non-ionic surfactants according to formula (VI) above include alkylphenol oxy ethylates such as ethoxylated p-isooctylphenol commercially available under the brand name TRITON™ such as for example TRITON™ X 100 wherein the number of ethoxy units is about 10 or TRITON™ X 114 wherein the number of ethoxy units is about 7 to 8. Still further examples include those in which $R^1$ in the above formula (VI) represents an alkyl group of 4 to 20 carbon atoms, m is 0 and $R^3$ is hydrogen. An example thereof includes isotridecanol ethoxylated with about 8 ethoxy groups and which is commercially available as GENAPOL®X080 from Clariant GmbH. Non-ionic surfactants according to formula (VI) in which the hydrophilic part comprises a block-copolymer of ethoxy groups and propoxy groups may be used as well. Such nonionic surfactants are commercially available from Clariant GmbH under the trade designation GENAPOL® PF 40 and GENAPOL® PF 80.

The amount of fluoropolymer solids in the dispersion may be upconcentrated as needed or desired to an amount between 30 and 70% by weight. Any of the known upconcentration techniques may be used including ultrafiltration and thermal upconcentration.

The invention is further illustrated with reference to the following examples without the intention to limit the invention thereto.

EXAMPLES

Test Methods

Determination of Solid Content
Determination of solid content was carried out subjecting the sample to a temperature up to 250° C. for 30 min.

Determination of Particle Size
The latex particle size determination was conducted by means of dynamic light scattering with a Malvern Zetazizer 1000 HAS in accordance to ISO/DIS 13321. Prior to the measurements, the polymer latexes as yielded from the polymerizations were diluted with 0.001 mol/L KCl-solution, the measurement temperature was 25° C. in all cases. The reported average is the Z-average particle diameter unless otherwise indicated.

MFI was measured according to ISO 12086.

SSG, Standard specific gravity, was measured according ASTM 4894-04

Fluorinated Emulsifiers Used:

| | |
|---|---|
| $C_3F_7$—O—CF(CF$_3$)—CF$_2$—O—CHF—COOH | Compound 1 |
| CF$_3$—O—CF$_2$—CF$_2$—CF$_2$—O—CHF—CF$_2$—COONH$_4$ | Compound 2 |
| CF$_3$—O—CF$_2$—CF$_2$—CF$_2$—O—CHF—COONH$_4$ | Compound 3 |
| C$_3$F$_7$—O—CHF—CF$_2$COONH$_4$ | Compound 4 |
| C$_3$F$_7$—O—CHF—COONH$_4$ | Compound 5 |

Synthesis of Compound 1: $C_3F_7$—O—CF(CF$_3$)—CF$_2$—O—CHF—COOH

Perfluoro-5-methyl-3,6-dioxanonene-1 was added to an aqueous solution of KOH, LiOH and Aliquat™ 336 (trioctyl methyl ammonium chloride). The mixture was heated under reflux for 4 hours. Unreacted vinyl ether was distilled off and the alkaline aqueous phase was acidified with sulphuric acid. Methanol was added and the mixture was distilled. The distillate separated into two phases. The lower phase was distilled to yield the methyl ester of 2-H-perfluoro-5-methyl-3,6-dioxanonanoic acid (bp 98° C., 110 Hectopascal). The ester was converted to the ammonium salt by heating with excess aqueous ammonia. After removal of the methanol and surplus ammonia via distillation, a clear aqueous solution was obtained. On cooling, a part of the ammonium salt precipitated from the solution.

Synthesis of Compound 2: CF$_3$O(CF$_2$)$_3$OCHFCF$_2$COONH$_4$ a. Preparation of CF$_3$O(CF$_2$)$_3$OCHFCF$_2$CH$_2$OH Using a 2 liter glass flask equipped with a stirrer, thermometer, reflux condenser, and dropping funnel, 255 g of perfluoromethoxypropyl vinyl ether and 730 g methanol were converted with Rongalit® (sodium hydroxymethyl sulfinate) and t-butylhydroperoxide as radical source. Reaction temperature started at 47° C. and reached 64° C. at the end. Work up by distillation yielded 166 g of pure CF$_3$O(CF$_2$)$_3$OCHFCF$_2$CH$_2$OH with a boiling point of 60-61° C./20 mbar. This corresponds to a yield of 59%.

b. Preparation of CF$_3$O(CF$_2$)$_3$OCHFCF$_2$COONH$_4$

A 2 liter glass flask equipped with a thermometer, reflux condenser, dropping funnel and stirrer was used. 159 g of CF$_3$O(CF$_2$)$_3$OCHFCF$_2$CH$_2$OH, 520 g water, and 100 g sulfuric acid were added to the flask. 190 g KMnO4 were added manually to the liquid over a period of 2 hours while stirring. The reaction temperature increased to 95° C. over time. After a post reaction time of two hours, an aqueous solution of sodium bisulfite was added until a clear solution was formed. 100 g of methanol and in total 400 g of 50% aqueous sulphuric acid were added. Flash distillation of the reaction mixture resulted in a two phase distillate. Fractionation of the lower phase (120 g) gave 85.5 g of CF$_3$O(CF$_2$)$_3$OCHFCF$_2$COOCH$_3$ (bp 34-35° C./6 mbar; yield 50%). The ester was converted to the ammonium salt by saponification with aqueous ammonia and subsequent removal of methanol by distillation.

Synthesis of Compound 3: CF$_3$OCF$_2$CF$_2$CF$_2$OCHFCOONH$_4$

A glass flask equipped with a reflux condenser, thermometer, and magnetic stirrer was used. Perfluoromethoxy propyl vinyl ether (498 g), t-butanol (149 g), water (1007 g), potassium hydroxide (280 g), and methyl trioctyl ammonium chloride (10 g) were added to the flask. The resulting two phase mixture was heated to reflux for 16 hours under vigorous stirring. The mixture was cooled to room temperature and sulphuric acid (588 g) was added. The two phase mixture was heated again under vigorous stirring. At about 70° C. gas began to evolve. Heating was continued until the gas evolution ceased. The reflux condenser was replaced by a distillation device which allowed the separation of a lower phase while returning the upper phase to the flask. Methanol (150 g) was added and the mixture was heated for distillation. Distillation was carried out at ambient pressure without any intent for rectification. The condensed vapors separated into two phases. The lower phase was collected and the upper phase was returned to the flask. Distillation was continued until no more lower phase separated from the condensate. The combined crude ester (493 g) was purified by fractionated distillation, resulting in 401 g CF$_3$O(CF$_2$)$_3$OCHFCOOCH$_3$ with a boiling point of 51 to 52° C./22 mbar. This corresponds to a yield of 78%, based on vinyl ether used. The ester was converted to the ammonium salt by heating with aqueous ammonia and removal of methanol by fractionated distillation.

Alternatively, the previous reaction was repeated but 36 g of an aqueous solution containing 11 g of CF$_3$O(CF$_2$)$_3$OCHFCOONH$_4$ was used as phase transfer catalyst instead of methyl trioctyl ammonium chloride. The mixture was slowly heated to 70° C. internal temperature. Total reaction time was 26 hours. Work up was carried out as described above. 438 g of distilled $CF_3O(CF_2)_3OCHFCOOCH_3$ was received. This corresponds to a yield of 83% (calculation includes the amount of phase transfer catalyst).

The conversion to the ammonium salt was carried out as above.

Synthesis of Compound 4: $C_3F_7OCHFCF_2COONH_4$ a. Preparation of $CF_3CF_2CF_2OCHFCF_2CH_2OH$ In a 2 liter glass flask equipped with a stirrer, thermometer, reflux condenser, and dropping funnel were placed 1008 g methanol, 266 g perfluoropropyl vinyl ether, and 9.2 g of Rongalit® (sodium hydroxymethyl sulfinate). The reaction mixture was heated to reflux, resulting in an internal temperature of 29° C. 7.1 g t-butyl hydroperoxide (70% in water) was added in aliquots during a 9 h time frame. The internal temperature reached 52° C. at the end. The reaction mixture showed a single liquid phase and some solids. The liquid was analyzed by GC and indicated a content of 223 g of $C_3F_7OCHFCF_2CH_2OH$ which corresponded to a yield of 75%. Distillation of the reaction mixture resulted in 171 g of product (bp 54° C./23 mbar) corresponding to an isolated yield of 57%.

b. Preparation of $C_3F_7OCHFCF_2COONH_4$

A 2 liter glass flask equipped with a thermometer, reflux condenser, dropping funnel and stirrer was used. 674 g water, 136 g KMnO4, and 38 g NaOH were placed in the flask. 169 g $C_3F_7OCHFCF_2CH_2OH$ were added to the well stirred mixture via the dropping funnel. The temperature was held below 50° C. Residual permanganate was destroyed by addition of a small amount of methanol. The resulting slurry was filtered to remove the $MnO_2$. After washing the filter cake with water, the combined filtrate was transferred to a distillation apparatus and acidified with 65 g of sulfuric acid. 100 g methanol was added and a flash distillation was started. The distillate formed two layers. The lower layer was separated and the upper layer returned to the distillation pot. In total 182 g lower layer were collected. Fractionation of the crude ester resulted in 137 g of $C_3F_7OCHFCF_2COOCH_3$ with a boiling point of 55-56° C./52 mbar. This corresponds to a yield of 77%. The ester was converted to the ammonium salt by saponification with aqueous ammonia and subsequent removal of methanol by distillation.

Synthesis of Compound 5:
$CF_3CF_2CF_2OCHFCOONH_4$

A 2 liter glass flask equipped with a mechanical stirrer, thermometer and reflux condenser (−80° C.) was used. Heating of the flask was provided by an electric heating mantle. The conversion was carried out as a one pot reaction. 275 g perfluoropropyl vinyl ether (PPVE), 280 g KOH, 602 g water, 151 g t-butanol, and 10 g methyl trioctyl ammonium chloride were placed in the flask. The three phase mixture was subjected to vigorous stirring. After initial heating a moderate exothermic reaction occurred. Mixing was continued for nine hours. During this time the internal temperature adjusted to 27-33° C. Mixing was stopped when the exothermic reaction ceased. The reaction mixture formed two layers. The low temperature reflux condenser was replaced by a standard reflux condenser. Sulfuric acid (392 g) was slowly added without external cooling. The batch was heated to reflux. Unreacted PPVE was vented. At about 80° C. internal temperature gas began to evolve. Heating was continued until the gas evolution had ceased. At this time the internal temperature reached 101° C. The batch was cooled to RT and the reflux condenser was replaced by a distillation device. No column was used. 110 g methanol was added to the batch and distillation was started. The condensed vapors formed two layers. The lower layer was separated and the upper layer was returned to the flask. Distillation was stopped when no more lower phase was formed. In total, 234 g of lower phase were collected. Fractionation of the lower phase yielded 167 g of $C_3F_7OCHFCOOCH_3$ with a boiling point of 120-122° C. at ambient pressure.

Calculated yield: 59% based on total PPVE used; 70% based on converted PPVE.

The ester was converted to the ammonium salt by reaction with aqueous ammonia. Methanol was removed by fractionated distillation. The resulting aqueous solution was used as an emulsifier in the polymerization of fluorinated monomers.

Comparative Example 1

Polymerization of Fluorinated Monomers with APFO 28 l deionized water containing 2 g ammonium perfluorooctanoic acid (APFO) were fed in a 50 l polymerization vessel together with 100 g NaOH and 36 mg $CuSO_4$. Air was removed by alternating evacuation and pressurizing with nitrogen up to 4 bar. Then the vessel was pressurized with 6.4 bar HFP, 5.2 bar VDF, 3.7 bar TFE and 0.1 bar ethane. The temperature in the vessel is adjusted to 70° C. Polymerization was initiated by pumping in the vessel an aqueous solution containing 36 g ammonium persulfate (APS) dissolved in 100 ml deionized water and a solution of 6 g $Na_2S_2O_5$ in 50 ml deionized water. The speed of agitation was 240 rpm. Polymerization temperature and pressure were kept constant by feeding TFE, HFP and VDF in a constant ratio of 1:0.455:0.855. When 3.5 kg TFE were consumed, polymerization was stopped by closing the monomer-feeding and lowering the speed of agitation. The vessel was vented and the resulting dispersion discharged. The thus obtained dispersion had a solid content of 23% and particle size (volume average diameter) of about 271 nm.

Example 1

Polymerization of Fluorinated Monomers Using Compound 1

28 l deionized water containing 2 g of compound 1 were fed in a 50 l polymerization vessel together with 100 g NaOH and 36 mg $CuSO_4$. Air was removed by alternating evacuation and pressurizing with nitrogen up to 4 bar. Then the vessel was pressurized with 6.4 bar HFP, 5.2 bar VDF, 3.7 bar TFE and 0.1 bar ethane. The temperature in the vessel was adjusted to 70° C. Polymerization was initiated by pumping in the vessel an aqueous solution containing 36 g APS dissolved in 100 ml deionized water and a solution of 6 g $Na_2S_2O_5$ in 50 ml deionized water. The speed of agitation was 240 rpm. Polymerization temperature and pressure were kept constant by feeding TFE, HFP and VDF in a constant ratio of 1:0.455:0.855. When 3.5 kg TFE were consumed, polymerization was stopped by closing the monomer-feeding and lowering the speed of agitation. The vessel was vented and the resulting dispersion discharged. The thus obtained dispersion had a solid content of 21% and particle size of about 243 nm (volume average diameter). The MFI (265° C./5 kg) was 0.04.

Examples 2 to 5

Polymerization of Fluorinated Monomers Using Compounds 2 to 5

In examples 2 to 5, polymerization of fluorinated monomers was done using compounds 2 to 5 respectively. The polymerization experiments were performed in a 40 l kettle equipped with an impeller agitator and a baffle. The kettle was charged with 30 l of deionized water and set to 35° C.; the kettle was evacuated repeatedly to remove oxygen. Agitation speed was set to 165 rpm. The oxygen free kettle was charged with 70 mmol fluorinated surfactant (compounds 2-5) as listed in table 3 and the following materials were added: 0.5 ml of a solution containing 40 mg of copper sulphate penta hydrate and 1 mg of conc. sulphuric acid; 15 g of a 25 w-% of aqueous ammonia solution and 5.6 g of $CF_3CF_2CF_2$—O—$CF(CF_3)$—CF2-O—CF=$CF_2$ (PPVE-2). Finally the reactor was pressurized with tetrafluoroethylene (TFE) to 0.2 MPa and 47 g of hexafluoropropylene (HFP) were added. The kettle was then set to 1.5 MPa using TFE and 100 ml of an aqueous initiator solution containing 140 mg of sodium disulfite followed by 100 ml of a solution containing 340 mg of ammonium peroxodisulfate was pumped into the reactor. The beginning of the polymerization was indicated by a pressure drop. During polymerization the pressure was maintained at 1.5 MPa by feeding TFE continuously. After 3.2 kg of TFE had been added, the monomer valve was closed and the pressure was released. The characteristics of the obtained polymer latices are summarized in table 1.

1000 ml of this polymer dispersion were coagulated by adding 20 ml hydrochloric acid under agitation. The coagulated material was agglomerated with gasoline and washed repeatedly. The agglomerated polymer was dried overnight at 200° C. in a vacuum oven; test data are given in table 1.

TABLE 1

| fluoropolymer test data | | | |
|---|---|---|---|
| | Ex | | |
| | 2 | 3 | 4 |
| Compound | 2 | 3 | 4 |
| Polymerization time (min) | 82 | 82 | 83 |
| Average Particle Size (nm) | 126 | 108 | 128 |
| SSG (g/cm³) | 2.168 | 2.167 | 2.164 |
| Solid content (w-%) | 10.2 | 10.3 | 10.2 |

Determination of Bio-Accumulation

The fluorinated surfactants were evaluated for urinary clearance using a pharmacokinetic study in rats. The goal was to measure the total amount of parent compound eliminated via urinary output and estimate the rate of elimination. The study was approved by the IACUC (Institutional Animal Care and Use Committees) and was performed in 3M Company's AAALAC (Association for Assessment and Accreditation of Laboratory Animal Care)—accredited facility.

The study utilized male Sprague Dawley rats, 6 to 8 weeks of age, and approximately 200 to 250 g body weight at study onset. The test compounds of table 2 were administered at a dose of 73 micro Moles per kg body weight in rats (N=3 animals per tested compound). All test compounds were prepared in sterile deionized water and given to rats via oral gavage. After test compounds administration, the rats were housed individually in metabolism cages for urine collection: 0 to 6 hours, 6 to 24 hours, 24 to 48 hours and 72 to 96 hours. Animals were observed throughout the study for clinical signs of toxicity. Gross necropsy was performed at the termination of each study (96 hours post-dose) with sera and liver samples being retained from each animal.

The concentration of the parent compound or metabolites thereof were quantitatively measured via fluorine NMR on each urine sample for each animal at each time point based on internally added standards.

The bioaccumulation data obtained in accordance with the above test are reported in table 2 below.

TABLE 2

| | T½ (h) | % Recovery (96 h) | Compound-related Effects |
|---|---|---|---|
| APFO | ~550 | 6 | Hepatomegaly |
| Compound 2 | 12 | 84 | — |
| Compound 3 | 11 | 95 | — |
| Compound 4 | 11 | 94 | — |

T ½ and % recovery are based on elimination of the major metabolite —$C_3F_7$—O—$CHFCOO^-$. $T_{1/2}$ is the renal half-life and is the time required for the amount of a particular substance in a biological system to be reduced to one half of its value by biological processes when the rate of removal is approximately exponential. In these examples the value of $T_{1/2}$ is calculated by exponential least squares curve fitting ($y=Ae^{Bx}$ and $T_{1/2}=0.693/B$) where y represents the concentration of analyte in urine and x represents time in hours.

What is claimed is:

1. A fluorinated surfactant having the general formula:

$$[R_f\text{—(O)}_t\text{—CHF—}(CF_2)_n\text{—COO}^-]_i X^{i+} \qquad (I)$$

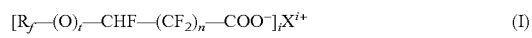

wherein t is 0 and wherein $R_f$ is a perfluorinated group of the formula $R_f^4$—$[OR_f^5]_k$—$[OR_f^6]_m$—O—$CF_2$— wherein $R_f^4$ is a perfluorinated aliphatic group of 1 to 6 carbon atoms, $R_f^5$ and $R_f^6$ each independently represents a linear perfluorinated alkylene of 1, 2, 3 or 4 carbon atoms and k and m each independently represent a value of 0 to 4 and wherein n is 0 or 1, $X^{i+}$ represents a cation having a valence i and i is 1, 2 or 3.

2. Method for making a fluoropolymer comprising an aqueous emulsion polymerization of one or more fluorinated monomers wherein said aqueous emulsion polymerization is carried out in the presence of one or more fluorinated surfactants as defined in claim 1.

3. Method according to claim 2 wherein the amount of said one or more fluorinated surfactants is between 0.001 and 5% by weight based on the amount of water in the aqueous phase of the aqueous emulsion polymerization.

4. Method according to claim 2 wherein said aqueous emulsion polymerization further comprises one or more fluorinated surfactants other than said fluorinated surfactants defined in claim 1.

5. Method according to claim 4 wherein said further fluorinated surfactants comprise perfluorinated polyether surfactants.

6. Aqueous composition comprising one or more fluorinated surfactants as defined in claim 1 in an aqueous medium.

7. Aqueous composition according to claim 6 wherein said aqueous composition comprises fluoropolymer particles.

8. Aqueous composition according to claim 7 wherein said fluoropolymer particles have an average diameter of 40 to 400 nm.

9. Aqueous composition according to claim 7 wherein the amount of fluoropolymer particles is between 15 and 70% by weight.

10. Aqueous composition according to claim 7 further comprising a non-ionic non-fluorinated surfactant.

11. Method comprising applying an aqueous composition as defined in claim 7 to a substrate.

* * * * *

UNITED STATES PATENT AND TRADEMARK OFFICE
CERTIFICATE OF CORRECTION

PATENT NO. : 7,838,608 B2
APPLICATION NO. : 11/612502
DATED : November 23, 2010
INVENTOR(S) : Klaus Hintzer It is certified that error appears in the above-identified patent and that said Letters Patent is hereby corrected as shown below:

On the Title Page, Column 2 (Other Publications)
Line 1, delete "Nucleophiicity" and insert in place thereof -- Nucleophilicity --.

On the Title Page, Column 2 (Assistant Examiner)
Line 1, delete "Nicol" and insert in place thereof -- Nicole --.

On Title Page 3, Column 1 (Foreign Patent Documents)
Line 35, delete "2004-359397" and insert in place thereof -- 2004-358397 --.

On Title Page 3, Column 2 (Other Publications)
Line 9, delete "Technology." and insert in place thereof -- Technology, --.

Line 26, delete "Emulusion" and insert in place thereof -- Emulsion --.

Line 29, delete "Perfluroporpoxyethylene" and insert in place thereof
-- Perfluoropropoxyethylene --.

Line 48, delete "Perfluorvinyl" and insert in place thereof -- Perfluorovinyl --.

Column 6
Line 3, delete "hydolysis" and insert in place thereof -- hydrolysis --.

Column 7
Line 18, delete "thereof," and insert in place thereof -- thereof; --.

Column 8
Line 66-67, delete "$CF_3$-$(CF_2)_2$-O-$CF(CF_3)$-$CF_2$-O-$F(CF_3)$-$CF_2$-O-CF=$CF_2$." and
insert in place thereof -- $CF_3$-$(CF_2)_2$-O-$CF(CF_3)$-$CF_2$-O-$CF(CF_3)$-$CF_2$-O-CF=$CF_2$. --.

Signed and Sealed this
Seventeenth Day of May, 2011

David J. Kappos
*Director of the United States Patent and Trademark Office*

Column 13

Line 10, delete "$CF_3CF_2CF_2OCHFCF_2CH_2O$ H" and insert in place thereof
-- $CF_3CF_2CF_2OCHFCF_2CH_2OH$ --.

Line 15, delete "-CF2-O-" and insert in place thereof -- $-CF_2-O-$ --.